United States Patent
Edvinsson et al.

(10) Patent No.: US 10,428,011 B2
(45) Date of Patent: *Oct. 1, 2019

(54) PROCESS TO PREPARE HIGHER ETHYLENE AMINES AND ETHYLENE AMINE DERIVATIVES

(71) Applicant: Akzo Nobel Chemicals International B.V., Arnhem (NL)

(72) Inventors: Rolf Krister Edvinsson, Partille (SE); Eike Nicolas Kantzer, Uddevalla (SE); Per Fredrik Olmo Larsson, Göteborg (SE); Karl Fredrik Lake, Södertälje (SE); Antoon Jacob Berend Ten Kate, Arnhem (NL)

(73) Assignee: Nouryon Chemicals International B.V., Arnhem (NL)

(*) Notice: Subject to any disclaimer, the term of this patent is extended or adjusted under 35 U.S.C. 154(b) by 0 days.

This patent is subject to a terminal disclaimer.

(21) Appl. No.: 16/074,496

(22) PCT Filed: Feb. 10, 2017

(86) PCT No.: PCT/EP2017/052948
§ 371 (c)(1),
(2) Date: Aug. 1, 2018

(87) PCT Pub. No.: WO2017/137532
PCT Pub. Date: Aug. 17, 2017

(65) Prior Publication Data
US 2019/0031597 A1 Jan. 31, 2019

(30) Foreign Application Priority Data
Feb. 12, 2016 (EP) .................... 16155549

(51) Int. Cl.
| | | |
|---|---|---|
| C07C 209/62 | (2006.01) | |
| C07C 273/18 | (2006.01) | |
| C07C 209/16 | (2006.01) | |
| C07C 269/06 | (2006.01) | |
| C07C 275/14 | (2006.01) | |
| B01D 53/62 | (2006.01) | |
| C07C 211/14 | (2006.01) | |
| C07D 263/20 | (2006.01) | |

(52) U.S. Cl.
CPC .......... *C07C 209/62* (2013.01); *C07C 209/16* (2013.01); *C07C 269/06* (2013.01); *C07C 273/1809* (2013.01); *C07C 273/1836* (2013.01); *C07C 273/1854* (2013.01); *C07C 273/1863* (2013.01); *B01D 53/62* (2013.01); *C07C 211/14* (2013.01); *C07C 275/14* (2013.01); *C07D 263/20* (2013.01); *Y02P 20/152* (2015.11)

(58) Field of Classification Search
None
See application file for complete search history.

(56) References Cited

U.S. PATENT DOCUMENTS

| | | |
|---|---|---|
| 2,812,333 A | 11/1957 | Steele |
| 4,111,840 A | 9/1978 | Best |
| 4,123,462 A | 10/1978 | Best |
| 4,387,249 A | 6/1983 | Harnden et al. |
| 4,503,250 A | 3/1985 | Herdle |
| 4,568,745 A | 2/1986 | Ghelli et al. |
| 4,650,906 A | 3/1987 | Murakami et al. |
| 4,683,337 A | 7/1987 | Budde |
| 4,684,729 A | 8/1987 | Duquette et al. |
| 4,897,480 A | 1/1990 | Schoenleben |
| 5,112,984 A | 5/1992 | Richey, Jr. et al. |
| 5,262,534 A | 11/1993 | King |
| 5,364,971 A | 11/1994 | Su |
| 5,491,263 A | 2/1996 | Rooney et al. |
| 5,861,537 A | 1/1999 | Shinohara et al. |
| 8,188,318 B2 | 5/2012 | Petraitis et al. |
| 8,273,884 B2 | 9/2012 | King et al. |
| 8,383,860 B2 | 2/2013 | Cook et al. |
| 8,440,852 B2 | 5/2013 | Dahmen et al. |
| 8,513,435 B2 | 8/2013 | Baloche et al. |

(Continued)

FOREIGN PATENT DOCUMENTS

| | | |
|---|---|---|
| CH | 478 180 A | 9/1969 |
| EP | 0 075 935 A2 | 4/1983 |
| EP | 0 222 934 A1 | 5/1987 |
| EP | 1 654 214 B1 | 3/2007 |
| GB | 1 510 538 | 5/1975 |
| JP | S 52-85991 A | 7/1977 |
| JP | S 56-108534 A | 8/1981 |
| JP | S 58-69847 A | 4/1983 |
| JP | S60-120842 A | 6/1985 |
| JP | S60-126248 A | 7/1985 |

(Continued)

OTHER PUBLICATIONS

P.K. Shenoy et al., "2-Imidazolidinones (Ethylene Ureas)—A Review"; American Dyestuff Reporter; May 1968; p. 17-34.

(Continued)

*Primary Examiner* — Amy C Bonaparte
(74) *Attorney, Agent, or Firm* — Norris McLaughlin, P.A.

(57) ABSTRACT

The present invention relates to a process to prepare ethyleneamines of the formula $NH_2-(C_2H_4-NH-)_pH$ wherein p is at least 3 or derivatives thereof wherein one or more units $-NH-C_2H_4-NH-$ may be present as a cyclic ethylene urea unit or between two units $-NH-C_2H_4-NH-$ a carbonyl moiety is present, by reacting an ethanolamine-functional compound, an amine-functional compound in the presence of a carbon oxide delivering agent, wherein the molar ratio of ethanolamine-functional compound to amine-functional compound is at least 0.7:1 and the molar ratio of carbon oxide delivering agent to amine-functional compound is at least 0.05:1.

15 Claims, No Drawings

(56) References Cited

U.S. PATENT DOCUMENTS

| | | | |
|---|---|---|---|
| 8,618,108 | B2 | 12/2013 | King et al. |
| 8,907,088 | B2 | 12/2014 | King et al. |
| 9,321,007 | B2 | 4/2016 | Rochelle et al. |
| 2010/0094007 | A1 | 4/2010 | King et al. |
| 2010/0094008 | A1 | 4/2010 | King et al. |
| 2010/0121064 | A1 | 5/2010 | Dahmen et al. |
| 2012/0277435 | A1 | 11/2012 | King et al. |

FOREIGN PATENT DOCUMENTS

| | | |
|---|---|---|
| JP | 64-500357 A | 2/1989 |
| JP | 2012-504611 A | 2/2012 |
| WO | 2011/079008 A1 | 6/2011 |
| WO | 2013/110092 A1 | 7/2013 |
| WO | 2017/137530 A1 | 8/2017 |
| WO | 2017/137531 A1 | 8/2017 |

OTHER PUBLICATIONS

Namjoshi, et al.; "In Situ Synthesis of Useful Polyamines for $CO_2$ Capture From Piperazine"; AIChE Annual Meeting Conference 2012; 10 pages.

Lepaumier et al., "Study on the Degradation Mechanisms of New Amines in the Presence of $CO_2$ or $O_2$"; LMOPS; Jun. 15, 2009—Trondheim; 42 pgs.

Lepaumier et al., "New Amines for $CO_2$ Capture. I. Mechanisms of Amine Degradation in the Presence of $CO_2$"; Industrial & Engineering Chemistry Research 2009, vol. 48, pp. 9061-9067.

Lepaumier et al.; "New Amines for $CO_2$ Capture. II. Oxidative Degradation Mechanisms"; Industrial & Engineering Chemistry Research 2009, vol. 48, pp. 9068-9075.

Lepaumier et al.; "New Amines for $CO_2$ Capture. III. Effect of Alkyl Chain Length Between Amine Functions on Polyamines Degradation" Industrial & Engineering Chemistry Research 2010, vol. 49, pp. 4553-4560.

Huntsman Corporation Brochure; "Ethyleneamines: A Global Profile of Products and Services"; 2007; 76 pgs.

Brissault et al.; "Synthesis of Linear Polyethylenimine Derivatives for DNA Transfection" Bioconjugate Chemistry; vol. 14, No. 3, 2003; pp. 581-587.

Stapleton; "A Simple Method of Polyamine Purification"; Australian Journal of Chemistry 1985, vol. 38, pp. 633-666.

Global CCS Institute; "3.2 Thermal Degradation of MEA"; 4 pgs, downloaded Sep. 11, 2018.

CSIRO—Australian National Low Emissions Coal Research and Development; Project: Environmental Impacts of Amine-based $CO_2$ Post Combustion Capture (PCC) Process; 2012; 116 pgs.

International Search Report and Written Opinion for PCT/EP2017/052948 dated Mar. 24, 2017.

The Dow Chemical Company Brochure; "Ethyleneamines"; Aug. 2001; 48 pgs.

Davis ("Thermal Degradation of Aqueous Amines Used for Carbon Dioxide Capture" Ph.D. dissertation, 2009, The University of Texas at Austin, retrieved from http://rochelle.che.utexas.edu/files/2015/02/Davis-2009- Thermal-Degradation-of-Aqueous-Amines-Used-for-Carbon-Dioxide-Capture.pdf on Feb. 10, 2019) (Year: 2009).

PROCESS TO PREPARE HIGHER ETHYLENE AMINES AND ETHYLENE AMINE DERIVATIVES

This application is a national stage filing under 35 U.S.C. § 371 of PCT/EP2017/052948, filed Feb. 10, 2017, which claims priority to European Patent Application No. 16155549.5 filed Feb. 12, 2016, the contents of which are each incorporated herein by reference in their entireties.

The present invention relates to a process for making higher ethylene amines (EA), i.e. ethylene amines and derivatives (or precursors) thereof, like urea derivatives, that contain at least 3 ethylene units, by reacting an ethanolamine functional compound with an amine functional compound in the presence of a carbon oxide delivering agent.

Ethylene amines consist of two or more nitrogen atoms linked by ethylene units. Ethylene amines can be present in the form of linear chains $H_2N(-C_2H_4NH)_p-H$. For p=1, 2, 3, 4, . . . these are denoted EDA, DETA, L-TETA, L-TEPA, . . . .

With three or more ethylene units it is also possible to create branched ethylene amines such as $N(CH_2CH_2NH_2)_3$, TAEA. Two adjacent nitrogen atoms linked by two ethylene units are called a piperazine ring

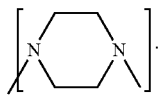

Piperazine rings can be present in longer chains to produce the corresponding cyclic ethylene amines.

Two adjacent nitrogen atoms linked by one ethylene unit and one carbonyl moiety form a cyclic ethylene urea (EU). An ethylene amine (EA) in which two nitrogen atoms are linked intramolecular by a carbonyl moiety

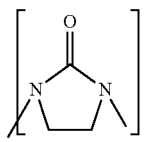

is here referred to as an UEA. Replacing the carbonyl bridge with two hydrogen atoms yields the corresponding ethylene amine. For example: EU⇔EDA, UDETA⇔DETA, UAEEA⇔AEEA, UTETA⇔L-TETA, UTEPA⇔L-TEPA. Some higher amines host more than one carbonyl moiety, e.g. DUTETA the diurea of L-TETA. The carbonyl moiety may link nitrogen atoms on two separate molecules. For example $H_2NC_2H_4NH-CO-NHC_2H_4NH_2$ and replacing the carbonyl moiety with two hydrogen atoms here yields two EDA.

Each amine function in ethylene amines and ethylene ureas can be primary, secondary or tertiary. Furthermore, a secondary amine can be linear (linear secondary amines, LSA) or cyclic (cyclic secondary amine, CSA).

In the presence of any Brønsted acid (such as water) ethylene amines (EA) can be protonated ($EAH^+$). If not otherwise stated the term amine in this document will include both the protonated and unprotonated form.

Some ethylene amines and urea derivatives thereof are shown below as an illustration. This can naturally be extended to include a.o. pentaamines, hexaamines and so on.

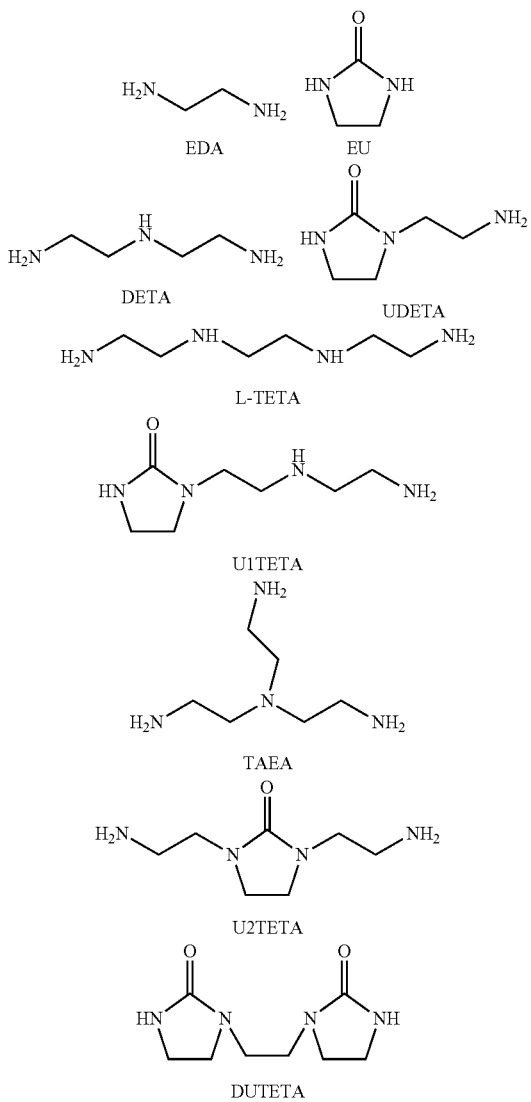

As to naming of the molecules, EDA stands for ethylenediamine, DETA for diethylenetriamine, TETA for triethylenetetraamine, TEPA for tetraethylenepentamine, PEHA for pentaethylenehexamine. When there is a single cyclic urea in the molecule this is indicated by adding a U in front of the name, i.e. UTETA means the cyclic urea of TETA, while when there are two cyclic ureas in the molecule this is indicated by DU, i.e. DUTETA means the internal cyclic diurea of TETA. If there is a number indicated for the U this refers to the amino group where the U group is located. There is one exception to this naming and that is that instead of UEDA the abbreviation EU is used, which stands for ethyleneurea. Furthermore, TAEA stands for trisaminoethylamine.

The manufacturing of ethylene amines is presently dominated by two routes. These are the reductive amination of MEA and the EDC route.

Reductive amination of MEA proceeds in the presence of a hydrogenation/dehydrogenation catalyst in an excess of ammonia. Next to the reductive amination of MEA to give EDA a number of side reactions including transamination produce a mixture of a large number of ethylene and ethanolamines. The output is dominated by mono and diethylene products (EDA, DETA, PIP and AEEA). Higher ethylene and ethanolamines are also formed but the mixture is complex and ineffective in producing high yields of the most important higher ethylene amines TETA and TEPA.

Several attempts to use transamination to produce ethylene amines with two or more ethylene units have been reported but seem limited to the diethylene compound DETA and have not been competitive to the EDC route described further below. See for example U.S. Pat. No. 8,383,860 B2; U.S. Pat. No. 8,188,318 B2; EP1654214B1 and U.S. Pat. No. 4,568,745.

The EDC route is the substitution reaction of EDC (ethylene dichloride) with ammonia and/or another ethylene amine at elevated temperatures and pressures to form hydrochlorides which are then reacted with caustic to generate mixtures of ethylene amines and NaCl.

Today, the EDC-based process is the main process for producing higher polyethylene polyamines. By higher ethylene amines we refer to those containing three or more ethylene units. AEP is an example of a triamine. Higher amines usually exist in so-called technical mixtures. For example, there are several tetramines possible and their technical mixture which is referred to as TETA typically comprises L-TETA, TAEA, DAEP, PEEDA. Similarly TEPA refers to a mixture of pentaamines (linear, branched and piperazine containing).

The EDC route apart from it being fully dependent on the use of ethylene dichloride which is toxic, highly flammable and carcinogenic expensive, difficult to handle and therefore not always and everywhere available has as a disadvantage that it has a low selectivity towards specific higher ethylene amines, as it gives a mixture of many different polyethylene amines. Furthermore the EDC route results in the creation of a lot of NaCl which in embodiment results in corrosion and colored products thereby creating a need for additional purification steps like distillation or bleaching.

U.S. Pat. No. 4,387,249 discloses the reaction of ethylenediamine (EDA), ethanolamine (MEA) and urea to give aminoethylethyleneurea (UDETA) and ethyleneurea (EU) that after hydrolysis with NaOH(aq) gives diethylenetriamine (DETA) and ethylenediamine (EDA).

U.S. Pat. No. 5,491,263 discloses that oxazolidinones can react with secondary amines or alkanol amine to produce substituted ethylenediamines. Products that are generally mentioned are EDA, DETA, TETA, TEPA, PEHA, PIP. Notably none of these can be formed from the reaction of an oxazolidionone and a secondary amine or alkanol amine. It is indicated that the oxazolidinone can be generated by reacting an alkanolamine with urea. In an Example, a reaction of ethanolamine and urea and aminoethylpiperazine (AEP) is shown to result in the formation of diaminoethylpiperazine (DAEP). The urea compound is added in a low amount of 0.25 molar equivalent on the amine-functional reactant AEP.

U.S. Pat. No. 4,503,250 discloses the preparation of linear triethylene tetraamine L-TETA by reacting aminoethylethanolamine (AEEA) with EDA and a carbonic acid derivative (i.e. a carbon oxide delivering agent). It is said that the carbonic acid derivative can be a compound formed by earlier addition of an amine or alcohol to carbon dioxide. Though the document states in general that the components may be used in any amount, it suggests that the carbonic acid derivative functions as a catalyst and in all examples the carbonic acid derivative is used in a small amount. In the Examples, entry 5, AEEA is reacted with imidazolidinone (i.e a carbonic acid derivative of EDA) to give L-TETA, however in this Example the amount of carbon oxide delivering agent is very low, only around 0.3 equivalent on total amine compound (i.e. total EDA present in the imidazolidinone and as EDA) and the amount of ethanolamine-functional compound on amine-functional compound was similarly low at around 0.3 equivalent. Another example mentions that oxazolidinone (i.e. the carbonic acid derivative of ethanolamine) is reacted with DETA to give a small amount of TETA (entry 8 in the Tables) again because very little carbon oxide delivering agent, and ethanolamine compound, less than 0.5 equivalent, was used per mole of DETA. AEEA with urea was found to give DETA (entry 7 in the Tables) and also a small amount of TETA. For some embodiments it is indicated that the product mixture was only obtained after hydrolysis. Accordingly, in this whole '250 document the yield of higher ethylene amines is very low and subject to improvement.

Nowadays there is a high demand for higher ethylene amines and hence there is a need for a process for selectively making such higher ethylene amines with an improved yield. Especially there is a need for a process to prepare specific higher linear ethylene amines with good yield and selectivity. Furthermore there is a need for such a process for making higher ethylene amines that does not co-generate large amounts of waste salt.

The present invention now provides a process to prepare ethyleneamines of the formula $NH_2$—$(C_2H_4$—$NH$—$)_pH$ wherein p is at least 3 or derivatives thereof wherein one or more units —$NH$—$C_2H_4$—$NH$— may be present as a cyclic ethylene urea unit

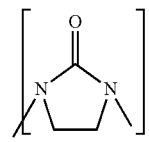

or between two units —$NH$—$C_2H_4$—$NH$— a carbonyl moiety

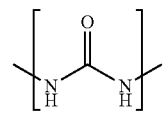

may be present, by reacting an ethanolamine-functional compound, an amine-functional compound in the presence of a carbon oxide delivering agent, wherein the molar ratio of ethanolamine-functional compound to amine-functional compound is at least 0.7:1 and the molar ratio of carbon oxide delivering agent to amine-functional compound is at least 0.05:1.

It was found that when adding at least 0.7 molar equivalents of ethanolamine-functional compound to amine-functional compound and at least 0.05 molar equivalents of carbon oxide delivering agent on amine-functional compound, the yield of higher ethylene amines increases considerably and also the amount of side products decreases, i.e. the selectivity of the reaction towards producing specific higher ethylene amines increases.

Preferably, the molar ratio of ethanolamine-functional compound to amine-functional compound is between 0.8 and 5:1 and the molar ratio of carbon oxide delivering agent to amine functional compound is between 0.2:1 and 20:1, even more preferably, the molar ratio of ethanolamine-functional compound to amine-functional compound is between 1:1 and 2:1 and the molar ratio of carbon oxide delivering agent to amine-functional compound is between 0.7:1 and 3:1. Most preferably the ethanolamine-functional compound is used slightly more than equimolar on basis of the amine-functional compound, such as at least in a ratio of 1.05:1 or even better at least 1.1:1

It should be noted that compounds exist that contain more than one carbonyl group that can be released from the molecule for transfer to the ethanolamine-functional compound, such as for example DUTETA. When determining the molar ratio for such compounds there should be an adjustment for the molar amount of carbon oxide they can release for transfer to the ethanolamine-functional compound. Accordingly, 1 mole of DUTETA should be considered 2 moles of carbon oxide delivering agent.

Selecting the right molar amounts of ethanolamine-functional compound and carbon oxide delivering agent on amine-functional compound was found to be essential for obtaining a good selectivity and yield in the process of the invention.

The molar amount of carbon oxide delivering agent on amine-functional compound is determined by the reactants in the process, independent of the dosing regime used for the reactants.

The reaction mixture is characterized by containing as reactants ethanolamine-functional compound, amine-functional compound and carbon oxide delivering agent and can be roughly represented by below non-limiting scheme.

alcohol function to an amine function without giving a chain extension can take place as well. The product (D) may undergo further reaction leading to secondary CO containing products as illustrated by reaction IV and product (F). Such products include but are not limited to cyclic ethylene urea derivatives but include all kinds of CO containing amines as for example illustrated in below examples of CO delivering agents. Optionally the CO groups can be removed leading to the formation of an ethylene amine (E).

The ethanolamine-functional compound is a compound containing one hydroxyl group linked via an ethylene to an amine group that optionally may be present as its carbamate equivalent. Generally the ethanolamine-functional compound is of the following formula

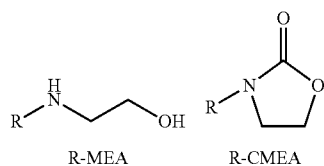

R-MEA    R-CMEA

Where R in embodiments is a substituted or unsubstituted alkyl group which also can contain unsaturated moieties and heteroatoms, such as oxygen and nitrogen.

Scheme I: Amine functional compound is a primary amine

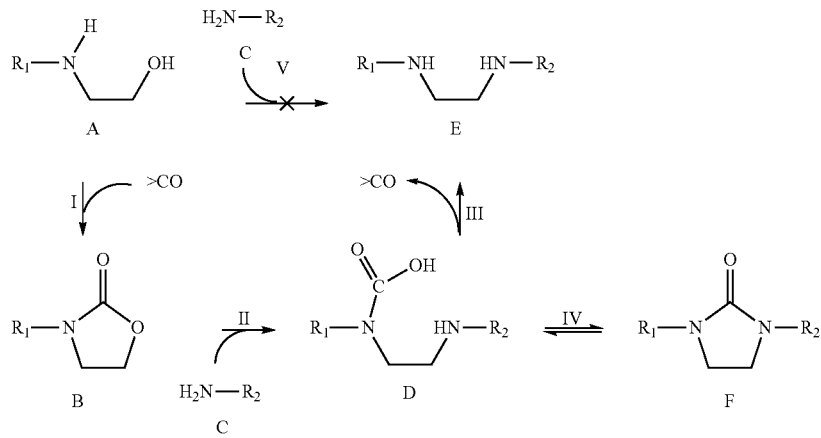

I Addition of CO to the ethanolamine to form the 2-oxazolidinone ring
II Chain extension by ring opening by primary amine
III Removal of carbonyl group to form the ethylene amine
IV Intramolecular rearrangement of carbonyl group
V Hypothetical direct uncatalyzed amination A number of reactions take place in parallel when heating a mixture of a carbonyl source, an ethanolamine-functional compound and an amine-functional compound.

Without being bound to theory this can be summarized in two main reaction steps each composed of multiple sub steps: 1) the activation of the alcohol function (A) by the carbonyl group, the oxazolidinone (B) is assumed to be an intermediate, 2) the activated alcohol function is replaced by an amine (C) to give a chain extended primary addition product (D). In the presence of ammonia a conversion of the Examples of ethanolamine functional compounds include

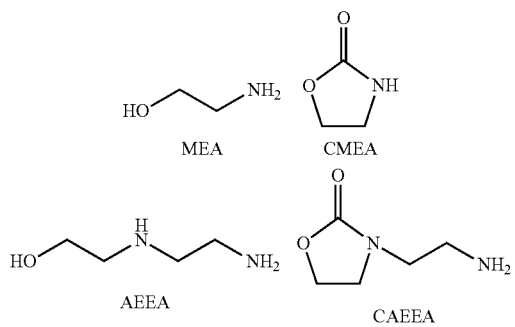

MEA    CMEA

AEEA    CAEEA

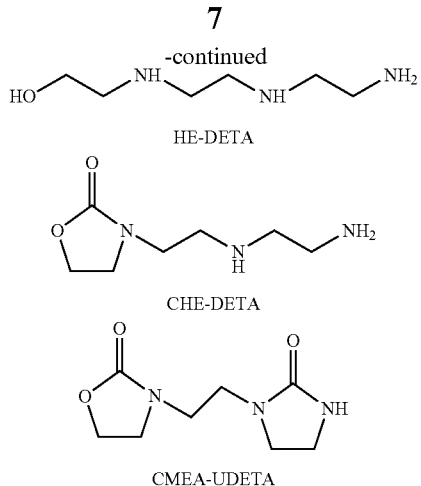

HE-DETA

CHE-DETA

CMEA-UDETA

As to naming convention, MEA stands for monoethanolamine, AEEA stands for aminoethylethanolamine (also referred to as hydroxyethylethylenediamine), HE-DETA for hydroxyethyldiethylenetriamine, and from there on HE-TETA for hydroxyethyl triethylenetetramine etc. By using the letter C it is indicated that a cyclic carbamate ring is present in the molecule The carbon oxide delivering agent is a compound containing a carbonyl moiety that can be transferred to an ethanolamine functional compound leading to the formation of a cyclic carbamate, such as CMEA (2-oxazolidinone) or that can be transferred to an ethylene amine (EA) leading to the formation of the corresponding cyclic ethylene urea (UEA). Next to cyclic compounds linear carbamates and ureas may form as well.

Carbon oxide delivering agents within the scope of the present invention include carbon dioxide, and organic compounds in which a carbonyl moiety is available for being transferred as described above. Organic compounds in which a carbonyl moiety is available include urea and derivatives thereof; linear and cyclic alkylene ureas, especially cyclic urea, mono or di-substituted alkylene ureas, alkyl and dialkyl ureas, linear and cyclic carbamates, organic carbonates and derivatives or precursors thereof.

Such derivatives or precursors may for example include ionic compounds such as carbonate or bicarbonate salts, carbamic acids and associated salts, that can be converted, in some embodiments in situ in the process of the invention, into their non-ionic counterparts, for example into linear and cyclic carbamate or urea compounds. When such ionic compounds are used in the present invention, they are organic hydrocarbon-based carbonate, bicarbonate or carbamate salts. Preferably the CO delivering agent is CO2 or an organic compound that is suitable for use as a carbon oxide delivering agent and wherein alkylene is ethylene, or urea or ethylene carbonate, more preferably the carbon oxide delivering agent is at least partly added as carbon dioxide or urea. The carbon oxide delivering agent can be present in the process in the same molecule as the amine functional or the ethanolamine functional compound by using the aforementioned urea or carbamate compounds.

Examples of carbon oxide delivering agents include

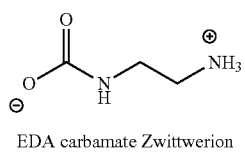

EDA carbamate Zwittwerion

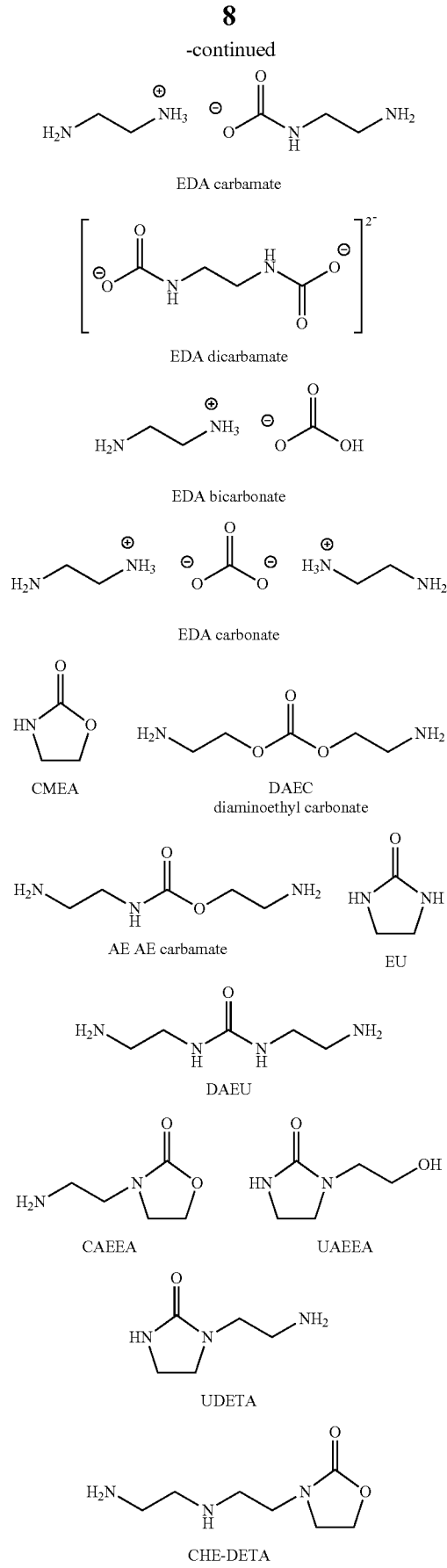

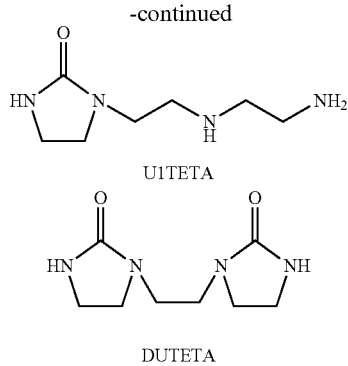

U1TETA

DUTETA

In the above drawing CAEEA again stands for the carbamate of aminoethylethanolamine, UDETA for the urea of diethylene triamine, DAEU stands for diaminoethyl urea, AE AE carbamate stands for amino ethyl aminoethanol carbamate, CHE-DETA stands for the carbamate of hydroxyethyldiethylene triamine, U1TETA stands for the terminal urea of triethylene tetramine, and DUTETA stands for the 1,3-diurea of triethylene tetramine.

The carbon oxide delivering agent is most preferably added to the reaction in the form of carbon dioxide, the carbamate derivative of the ethanolamine-functional compound or the urea derivative of the amine-functional compound, or a combination of these.

Heating a suitable mixture of an ethanolamine, an amine that is not tertiary and a carbon oxide delivering agent to a relatively high temperature provides a way to produce a higher amine and CO containing derivative thereof that can serve as a carbon oxide delivering agent.

The amine-functional compound is a compound containing one or more amine groups, preferably at least two amine groups, and no alcohol groups.

In a preferred embodiment the amine-functional compound is a compound containing at least two amine groups. Even more preferred the amine-functional compound contains at least two primary amine groups, and optionally more amine groups that may be primary, secondary and/or tertiary amines wherein the amine groups within the compound are linked to one another via ethylene groups, and optionally some by a carbonyl moiety (to give a urea unit in the amine functional compound).

In a further preferred embodiment in the process the ethanolamine-functional compound is of the formula OH—$(C_2H_4$—NH—$)_q$H wherein q is at least 1 and the amine-functional compound is of the formula $NH_2$—$(C_2H_4$—NH—$)_r$H wherein r is at least 1, wherein the sum of q+r is at least 3 and wherein optionally one or more q or r units may be present as a cyclic ethylene urea, or cyclic ethylene carbamate unit.

In another preferred embodiment the ethanolamine-functional compound and the carbon oxide delivering agent are at least partly added as one compound by using a carbamate adduct and/or the amine-functional compound and the carbon oxide delivering agent are at least partly added as one compound by using an urea adduct.

In a more preferred embodiment the ethanolamine-functional compound is AEEA, UAEEA, CAEEA or a mixture thereof and the amine-functional compound EDA, EU or a mixture thereof, or in another more preferred embodiment the ethanolamine-functional compound is MEA, CMEA or a mixture thereof and the amine-functional compound DETA, UDETA or a mixture thereof, or the ethanolamine-functional compound is MEA, CMEA or a mixture thereof and the amine-functional compound EDA, EU or a mixture thereof.

Even more preferred the ratio of AEEA, UAEEA+CAEEA to EDA+EU is equal to or higher than 1, respectively the ratio MEA+CMEA to DETA+UDETA is higher than 1, yet more preferred higher than 2, the ratio MEA+CMEA to EDA+EU is higher than 2, yet more preferred higher than 3.

In an embodiment the amine-functional compound and/or the ethanolamine-functional compound are obtained directly or indirectly from an amine production process as described above, such as for example a reductive amination process or EDC process.

The product mixture can be further processed or fractionated into several products that each independently are either pure compounds or mixture of compounds, some of which may be recycled.

The process of the present invention can be done with or without any additional liquid present. If a liquid is added to the reaction system, the liquid preferably is a polar liquid, such as an alcohol or water. Doing the process of the present invention in the presence of water as a liquid or without any additional liquid is preferred.

The reactor employed can be any suitable reactor including continuously stirred tank reactor, pipeline reactor, tubular or multi-tubular reactor. The reactor may be adiabatic or equipped with external or internal heating devices. Feed may be single point or split into multiple points. It can consist of multiple stages with inter-stage heat exchange.

The process is preferably performed at a temperature of at least 100° C. The temperature should preferably be lower than 400° C. More preferably the temperature is between 200 and 360° C. Even more preferably the temperature is between 230 and 340° C. Most preferably the temperature is between 250 and 310° C. In embodiments where the ethanolamine-functional compound is monoethanolamine the most preferred temperature range is between 230 and 290° C.

The reaction time during the process is in an embodiment between 5 minutes and 15 hours, preferably between 0.5 and 10 hours, more preferably between 1 and 6 hours.

The process can be carried out in one or multiple batch reactors, possibly in fed-batch operation, and/or in a continuously operating system in one reactor or in a cascade of continuous flow reactors, optionally with multiple feeding points. The reaction and separation can be performed in separate steps or at least partially simultaneously. The reaction and separation can involve multiple reaction steps with separation steps in between.

In the large-scale production of chemicals it is preferred to employ a continuous process. The continuous process may be, for example, a single-pass or a recycle process. In a single-pass process, one or more of the reagents pass through the process equipment once, and then the resulting effluent from the reactor is sent for purification or further processing.

The person skilled in the art is capable of selecting the proper reactor and separation unit scheme by determining the overall yield, energy consumption and waste production.

In yet another more preferred embodiment, aminoethylethanolamine (AEEA) and ethylenediamine (EDA), or MEA (monoethanolamine) and DETA (diethylenetriamine) are reacted with urea or CO2 as a carbon oxide delivering agent to form higher ethylene polyamines, mainly triethylenetetramine (TETA) and tetraethylenepentamine (TEPA):

EXAMPLES

Example 1 Reaction of AEEA with EDA and EU CO/Amine=1:1, OH/Amine=1:1.2

1 mole of AEEA was reacted with 1 mole of urea in an autoclave at 170° C. for 0.5 h. Analysis by gas chromatography using a flame ionization detector (GC-FID analysis) showed that 93% of AEEA had been converted to UAEEA. After venting the autoclave 1.2 mole of EDA and 0.2 mole of urea were added and the temperature was then increased to 280° C. and kept constant for 5 h. GC-FID analysis of the reaction mixture indicated 2.1% of L-TETA and 27.5% of UTETA (i.e. the sum of the three different UTETAs).

After cooling to room temperature 4.17 g of the reaction mixture were removed and hydrolysed with 4.11 g NaOH in 20 mL of water, at 200° C. for 1 h. Subsequent GC-FID analysis (water not included) of the liquid phases showed the formation of 32.2% L-TETA and 5.5% UTETAs.

Comparative Example 2 Reaction of AEEA with EDA and EU CO/Amine=1:1.8 OH/Amine=1:3

3 moles of EDA, 1 mole of AEEA and 1.65 moles of urea were reacted at 280° C. for 2 h in a closed pressure vessel. GC-analysis of the reaction mixture indicated 2.9% of L-TETA and 11.6% of UTETA (i.e. the sum of the three different UTETAs). After cooling to room temperature the mixture was then hydrolysed using 4 g of NaOH and 20 g of water at 200° C. for 1 h. GC-FID analysis (water not included) showed the liquid phases to contain 9.1% L-TETA and 2% UTETAs.

Comparative Example 3 Reaction of AEEA with EDA and EU CO/Amine=OH/Amine=1:3

1 mole of AEEA, 1 mole of EU and 2 moles of EDA were reacted at 300° C. for 6 h in a closed pressure vessel. GC-analysis of the reaction mixture indicated 2.4% of L-TETA and 18.8% of UTETA (i.e. the sum of the three different UTETAs).

After cooling to room temperature the mixture was then hydrolyzed using 4 g of NaOH and 20 g of water, at 200° C. for 1.5 h. GC-FID analysis (water not included) showed the formation of 15.3% L-TETA and 2.1% UTETAs.

Example 4 Reaction of AEEA with EDA and EU CO/Amine=2.1:1, OH/Amine=1:1

1 mole of AEEA and 1.1 mole of urea were reacted at 170° C. for 1.5 h in a closed pressure vessel. The reaction vessel was then allowed to cool to room temperature, at which point the lid was removed and 1 mole of EU was added. The resealed vessel was then heated to 280° C. and held at that temperature for 5 h.

For the hydrolysis 4 g of the reaction mixture was reacted with 4 g of NaOH in 20 g of water, at 200° C. for 1 h.

GC-FID analysis (water not included) showed the liquid phases to contain 22.4% of L-TETA and 27.5% UTETAs or in total 49.9% of L-TETA including urea precursors thereof.

Example 5 Reaction of DETA with CMEA at Different Molar Ratios

DETA was reacted with molar equivalents of CMEA ranging from 0.5 to 2.0 at 275° C. for 4 hrs in a closed pressure vessel. CMEA takes the dual role of ethanolamine and CO source and the ratios CO/amine and ethanolamine/amine is equal to the CMEA/DETA ratio. The weight fraction of the main components were determined by GC-FID analysis of the product mixture clearly shows that the yield of higher ethylene amines including their CO containing derivatives increase with the CMEA/DETA ratio. The tetraamines (TETA) dominate at all ratios. At higher ratios the relative amounts of pentaamines and higher (≥TEPA) increase as expected assuming a consecutive reaction between CMEA and the TETA initially formed.

| Reaction mixture after 4 hrs in wt %: | Examples: Moles CMEA/DETA (carbon oxide delivering agent/amine agent and ethanolamine agent/amine agent) in reactants | | | | | |
|---|---|---|---|---|---|---|
| | 0.5 | 0.8 | 1.0 | 1.2 | 1.5 | 2.0 |
| MEA | 12.0 | 7.7 | 5.0 | 2.7 | 1.2 | 0.0 |
| DETA | 35.2 | 15.4 | 10.2 | 6.5 | 2.9 | 1.3 |
| UDETA | 40.0 | 40.0 | 41.9 | 39.7 | 32.1 | 28.2 |
| MEA + DETA + UDETA | 87.3 | 63.1 | 57.1 | 48.8 | 36.2 | 29.5 |
| TETA | 8.8 | 24.5 | 24.1 | 26.8 | 34.2 | 35.0 |
| ≥TEPA | 0.6 | 3.9 | 8.6 | 11.5 | 17.9 | 24.3 |
| ≥TETA | 9.4 | 28.5 | 32.7 | 38.3 | 52.1 | 59.3 |

The invention claimed is:
1. A process to prepare
   ethyleneamines of the formula $NH_2$—$(C_2H_4$—$NH$—$)_pH$ wherein p is at least 3,
   derivatives of said ethyleneamines wherein one or more —NH—$C_2H_4$—NH— units are present as a cyclic ethylene urea unit

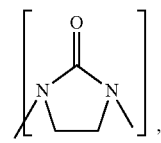

or
   derivatives of said ethyleneamines wherein a carbonyl moiety is present between two —NH—$C_2H_4$—NH— units,
   said process comprising the step of reacting an ethanolamine-functional compound with an amine-functional compound in the presence of a carbon oxide delivering agent, in which
      the ethanolamine functional compound contains a hydroxyl group linked via an ethylene group to an amine group, or its carbamate equivalent, or the ethanolamine functional compound is UAEEA (the urea of aminoethylethanolamine);
      the amine functional compound contains no alcohol groups, and contains at least two primary amine groups and optionally more primary, secondary and/or tertiary amine groups, wherein the amine groups are linked to one another via ethylene groups, and optionally by a carbonyl moiety;
      the carbon oxide delivering agent is carbon dioxide or an organic compound selected from urea, linear and cyclic alkylene ureas, mono- or di-substituted alkylene ureas, alkyl and dialkyl ureas, linear and cyclic carbamates, organic carbonates, and derivatives or precursors thereof selected from carbonate salts, bicarbonate salts and carbamic acids and their salts;

wherein the molar ratio of ethanolamine-functional compound to amine-functional compound is at least 0.7:1 and the molar ratio of carbon oxide delivering agent to amine-functional compound is between 0.8:1 and 20:1.

2. The process of claim 1 wherein the molar ratio of ethanolamine-functional compound to amine-functional compound is between 0.8 and 5:1.

3. The process of claim 1 wherein the molar ratio of ethanolamine-functional compound to amine-functional compound is between 1:1 and 2:1 and the molar ratio of carbon oxide delivering agent to amine-functional compound is between 0.8:1 and 3:1.

4. The process of claim 1 wherein the ethanolamine-functional compound and the carbon oxide delivering agent are at least partly added as one compound by using either said carbamate equivalent of the ethanolamine functional compound or UAEEA.

5. The process of claim 1 wherein the ethanolamine-functional compound is of the formula $OH-(C_2H_4-NH-)_qH$ wherein q is at least 1 and the amine-functional compound is of the formula $NH_2-(C_2H_4-NH-)_rH$ wherein r is at least 1, wherein the sum of q+r is at least 3 and wherein optionally one or more units $-NH-C_2H_4-NH-$ may be present as a cyclic ethylene urea unit, or one $-NH-C_2H_4-OH$ unit is present as a cyclic carbamate unit.

6. The process of claim 1, further comprising a step of converting derivatives of ethyleneamines of the formula $NH_2-(C_2H_4-NH-)_pH$ wherein p is at least 3 wherein one or more $-NH-C_2H_4-NH-$ units are present as a cyclic ethylene urea unit into ethyleneamines of the formula $NH_2-(C_2H_4-NH-)_pH$.

7. The process of claim 1 wherein the ethanolamine-functional compound is AEEA (aminoethylethanolamine), CAEEA (the carbamate of aminoethylethanolamine), UAEEA (the urea of aminoethylethanolamine) or a mixture thereof, and the amine-functional compound is EDA (ethylenediamine), EU, (ethyleneurea) or a mixture thereof.

8. The process of claim 7 wherein the molar ratio of the total of AEEA, UAEEA and CAEEA to the total of EDA and EU is equal to or higher than 1:1.

9. The process of claim 1 wherein the ethanolamine-functional compound is MEA (monoethanolamine), CMEA (the carbamate of monoethanolamine) or a mixture thereof and the amine-functional compound is DETA (diethylenetriamine), UDETA (the urea of diethylenetriamine) or a mixture thereof.

10. The process of claim 9 wherein the molar ratio of the total of MEA and CMEA to the total of DETA and UDETA is higher than 1:1.

11. The process of claim 1 wherein the ethanolamine-functional compound is MEA, CMEA or a mixture thereof and the amine-functional compound EDA, EU or a mixture thereof.

12. The process of claim 11 wherein the molar ratio of the total of MEA and CMEA to the total of EDA and EU, is higher than 2:1.

13. The process of claim 10 wherein the molar ratio of the total of MEA and CMEA to the total of DETA and UDETA is higher than 2:1.

14. The process of claim 12 wherein the molar ratio of the total of MEA and CMEA to the total of EDA and EU is higher than 3:1.

15. The process of claim 1 wherein the amine-functional compound is at least partly added as a urea derivative.

* * * * *